(12) United States Patent
Du et al.

(10) Patent No.: US 7,854,294 B2
(45) Date of Patent: *Dec. 21, 2010

(54) SOUND-ATTENUATING EARMUFF HAVING ISOLATED DOUBLE-SHELL STRUCTURE

(75) Inventors: Yu Du, Christianburg, VA (US); Kenji Homma, Blacksburg, VA (US); Michael A. Vaudrey, Blacksburg, VA (US)

(73) Assignee: Adaptive Technologies, Inc., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/691,821

(22) Filed: Jan. 22, 2010

(65) Prior Publication Data

US 2010/0218775 A1    Sep. 2, 2010

Related U.S. Application Data

(63) Continuation of application No. 11/949,850, filed on Dec. 4, 2007, now Pat. No. 7,703,572.

(60) Provisional application No. 60/872,669, filed on Dec. 4, 2006.

(51) Int. Cl.
*H04R 25/00* (2006.01)
*H04R 25/02* (2006.01)
*A61B 7/02* (2006.01)
*A42B 1/06* (2006.01)
*A42B 1/08* (2006.01)

(52) U.S. Cl. .................. 181/129; 181/130; 181/135; 381/372; 2/209; 2/423

(58) Field of Classification Search .............. 181/129, 181/130, 135; 381/372; 2/209, 423
See application file for complete search history.

(56) References Cited

U.S. PATENT DOCUMENTS

| | | | | | |
|---|---|---|---|---|---|
| 2,989,598 | A | * | 6/1961 | Touger et al. | 181/206 |
| 3,602,329 | A | * | 8/1971 | Bauer et al. | 181/129 |
| 3,864,756 | A | * | 2/1975 | Desimone | 2/423 |
| 4,156,118 | A | * | 5/1979 | Hargrave | 381/372 |
| 4,572,323 | A | * | 2/1986 | Randall | 181/129 |
| 4,674,134 | A | * | 6/1987 | Lundin | 2/209 |
| 4,771,454 | A | * | 9/1988 | Wilcox, Jr. | 379/430 |
| 4,989,271 | A | * | 2/1991 | Sapiejewski et al. | 2/209 |
| 6,695,093 | B1 | * | 2/2004 | Falco | 181/135 |
| 6,856,690 | B1 | * | 2/2005 | Skulley | 381/371 |
| 7,703,572 | B2 | * | 4/2010 | Du et al. | 181/129 |

* cited by examiner

*Primary Examiner*—Jeffrey Donels
*Assistant Examiner*—Christina Russell
(74) *Attorney, Agent, or Firm*—The Marbury Law Group, PLLC (57) ABSTRACT

An earmuff assembly with a double-shell structure is disclosed for use with a sound-attenuating circumaural headset. The earmuff assembly comprises a cup-shaped outer shell mounted on a resilient outer sealing ring and a cup-shaped inner shell mounted on a resilient inner sealing ring. By means of the two sealing rings the outer and the inner shells are brought into abutment with the head surface around an ear of a wearer. Both shells are structurally rigid. The sound attenuation performance is maximized by isolating the inner shell from the outer shell.

6 Claims, 7 Drawing Sheets

SOUND-ATTENUATING EARMUFF HAVING ISOLATED DOUBLE-SHELL STRUCTURE

CROSS REFERENCE TO RELATED APPLICATIONS

This application is a continuation of application Ser. No. 11/949,850 filed Dec. 4, 2007, now U.S. Pat. No. 7,703,572, which application claims the benefit of provisional application 60/872,669 filed Dec. 4, 2006. The 60/872,669 and the Ser. No. 11/949,850 applications are incorporated by reference herein, in their entireties, for all purposes.

GOVERNMENT RIGHTS

This invention was made with Government support under contract N68335-08-C-0292 awarded by the Department of the Navy. The Government has certain rights in this invention. The U.S. Government has a paid-up license in this invention and the right in limited circumstances to require the patent owner to license others on reasonable terms as provided by the terms of contract N68335-08-C-0292 awarded by the Department of the Navy.

BACKGROUND

The disclosure generally relates to earmuffs having ear cups adapted to be used as circumaural hearing protectors. More specifically, this disclosure relates to earmuffs comprising dual ear cups with one cup being positioned entirely within and mechanically isolated from the other and ear seals for use with such earmuffs.

Circumaural earmuff devices are commonly used to protect against hearing damage or hearing loss in noisy environments where the unwanted sound levels are higher than safe limits. Compared to other types of hearing protectors, such as earplugs, earmuffs (i.e. circumaural) are usually preferred in single hearing protection applications as the major hearing protection device because they are easy to don and doff, reliable in attenuation, with less dependence on user training, skill and motivation, less sensitive to fitting, and capable of being used as a one-size-fits-all device. Earmuff devices known in the prior art generally include a pair of ear cups made of rigid plastic materials. Each ear cup is typically single walled and lined with an acoustical material in the interior to help dampen and absorb sound energy. The two ear cups are mounted on the ends of a spring-like headband that provides a clamping force to keep the ear cups in contact with the wearer's head. A soft ear cushion (i.e. ear seal) having a concentric ring shape and with a certain thickness is interposed between the ear cup and the wearer's head for comfort purposes as well as to form, ideally, an airtight seal around the ear. Maximum sound attenuating capabilities are constantly pursued by developers to provide optimal protection against noise exposure.

At lower frequencies, such as below 1,000 Hz where the sound wavelength is considerably larger than the dimensions of the earmuff, the ear cup in the earmuff assembly is displaced, by the acoustic energy, as a rigid mass vibrating against the wearer's head through the soft cushion. That is, the ear cup can be considered as a single-degree-of-freedom (SDOF) vibration system at low frequencies where the acoustic pressure underneath the ear cup is proportional to the amplitude of the ear cup displacement. Therefore, at the low frequency range, the sound attenuation performance of the earmuff substantially depends on the ear cup volume, mass, headband clamping force and ear cushion stiffness. Many attempts have been made at increasing the sound attenuation of earmuff devices of the kind described above, i.e. the earmuffs with single-walled cups, by increasing the cup mass/volume and increasing the headband clamping force to tighten the fit of the ear cushions as well as to increase the cushion stiffness.

At higher frequencies, such as above 1,000 Hz, the sound wavelength becomes comparable or even smaller than the earmuff dimensions, and the ear cup flexural modes are excited by the acoustic energy. The sound attenuation performance of the earmuff is then largely determined by the structural rigidity and acoustical resonances inside the cavity enclosed by the ear cup and the wearer's head. Accordingly, many attempts have been made to increase the high frequency sound attenuation performance of earmuff devices by increasing the ear cup's structural stiffness and/or the acoustical damping inside the cup cavity. In addition, many other attempts have also been made at increasing the earmuff comfort and minimizing air leak by various ear seal designs that are for use with, particularly, earmuffs having single-walled cups.

Although these attempts may have resulted in certain increases in attenuation, the resulting increase in attenuation is limited by practical considerations in terms of comfort since adding cup mass, volume and headband clamping force, increasing cushion stiffness and structurally stiffening the cup usually raise the discomfort level. Further, the resulting increase in attenuation is also limited by physical laws associated with earmuff structures with single-walled cups. Sound attenuation provided by earmuffs is generally 10-30 dB for lower frequencies such as below 1,000 Hz, and 25-40 dB for higher frequencies such as above 1,000 Hz. These attenuation levels may not be sufficient for certain environments, such as the vicinity of jet engines of military and commercial aircrafts and extremely loud industrial or manufacturing plants where a very high sound attenuation is desired from earmuff devices.

Therefore, what would be useful would be a new earmuff design that not only is able to provide significantly improved sound attenuation performance compared to other circumaural earmuffs of the similar kind known in prior art, but also is able to offer sufficient comfort for practical use.

SUMMARY

In accordance with an embodiment, a sound-attenuating earmuff assembly is provided, comprising a cup-shaped outer shell mounted on a resilient outer sealing ring and a cup-shaped inner shell mounted on a resilient inner sealing ring. Both shells are made of structurally rigid engineering materials, for example, plastic. The two sealing rings are interconnected through a thin skin layer of soft compliant material. The outer shell is provided with means for mounting the earmuff assembly to a headband. An air gap is defined between the inner surface of the outer shell and the outer surface of the inner shell. In an embodiment, the inner shell is suspended to the outer shell through a resilient pad located in the air gap. In another embodiment, the resilient pad is removed to minimize the mechanical connecting paths between the inner shell and the outer shell, leaving the flexible thin skin layer between the two sealing rings being the only mechanical connection between the inner shell and the outer shell.

Due to the isolated double-shell structure of the earmuff, external noise which gives rise to vibrations directly in the outer shell will be attenuated considerably and more efficiently than would be the case for the single-walled earmuffs.

The reasons for this are twofold. First, the isolated double-shell structure acts as a two-degree-of-freedom (DOF) vibration system. At frequencies above the system resonances, the two-DOF system doubles the vibration attenuation rate offered by the single-walled earmuff structure which can be considered as a SDOF vibration system. Based on practical parameters of typical earmuffs, the system resonance frequencies of either a single-walled earmuff known in the prior art or a double-shelled earmuff disclosed herein is usually less than 400 Hz. This means that, compared to the conventional single-walled earmuff, a double-shelled earmuff can significantly improve the sound attenuation performance at frequencies above 400 Hz and up to about 1,000 Hz because the sound attenuation performance of earmuff devices is directly proportional to the vibration levels corresponding to the rigid-body motion of the earmuff in that frequency range. Second, the existence of the air gap between the outer shell and the inner shell provides an acoustic impedance mismatch in the sound traveling path, which offers enhanced acoustical insulation against the penetration of external noise. This effect is most effective at high frequencies, e.g. >1,000 Hz.

In accordance with another embodiment, a resilient ear seal particularly suited for an earmuff including two cup-shaped shells is provided, comprising an outer sealing ring adapted to support the outer shell of the earmuff and an inner sealing ring adapted to support the inner shell of the earmuff. Each sealing ring includes an outer peripheral side surface, an inner peripheral side surface that provides an opening around an ear of the wearer, an annular retainer plate for securing the sealing ring to the corresponding shell and an annular exposed surface opposite the retainer plate, which is adapted to contact the wearer's head. On the one hand, the two sealing rings are connected by a flexible thin skin layer which is vented to allow airflow; on the other hand, the two sealing rings are also mechanically isolated by the flexible thin skin layer since vibrations presented by the outer shell and the attached outer sealing ring can not be transmitted to the inner sealing ring and the attached inner shell through the flexible thin skin layer due to its negligible shear stiffness. In one embodiment, the flexible thin skin layer prevents the inner shell from falling out of the outer shell in the earmuff assembly. In another embodiment, the flexible thin skin layer, being stretched in the working position when the earmuff is worn by a user, provides clamping force to the inner shell to keep the inner shell in contact with the wearer's head.

DETAILED DESCRIPTION

Figure 1:
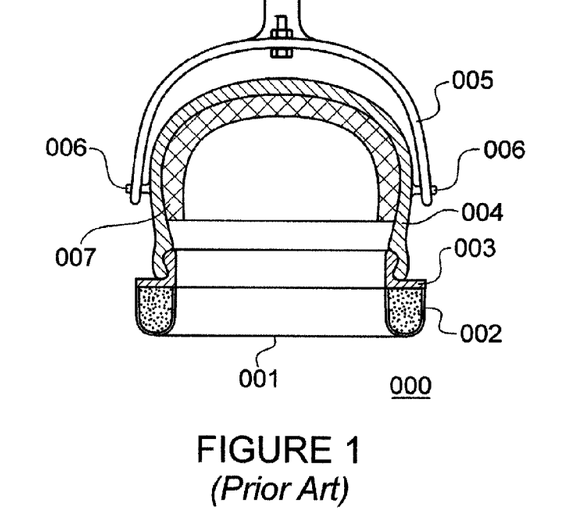
FIG. 1 illustrates a sound-attenuating earmuff assembly of the prior art, comprising a cup-shaped rigid shell mounted on a headband, interiorly lined with an acoustic foam insert, and seated on a single ring ear seal.

FIG. 1 shows a cross-sectional view of an earmuff assembly 000 comprising a single-walled cup for blocking the sound, which is commonly disclosed in the prior art. The single-walled cup 004 is rigid and mounted to a headband 005 through a mounting mechanism such as the pivot pins 006. The single-walled cup 004 is further lined with a layer of acoustic foam insert 007 interiorly. An annular ring-shaped ear seal 001 comprising a flexible sheath 002 is secured to the peripheral edge of the single-walled cup 004 through fastening means such as the retainer plate 003. The annular flexible sheath 002 encloses and is in communication with cushioning material, for instance, soft foam, silicon gel or a combination of both. When being worn, the ear seal 001 is compressed, under the static clamping force provided by the headband 005, to keep in contact with the head surface around an ear of the wearer. Therefore, a barrier between the ear and the external noise source is formed. For clarity, an earmuff having a single-walled ear cup is referred to herein as a "conventional earmuff." Similarly, an ear seal that is designed primarily for use with the conventional earmuff and comprises a single sealing ring is referred to herein as a "conventional ear seal."

The sound attenuation performance of an earmuff is normally evaluated using a subjective test method described by the ANSI standard S3.19-1974. It will be understood by those skilled in the art that, in accordance with ANSI S3.19-1974, the mean attenuation values provided by conventional earmuffs typically range from 10-30 dB at lower frequencies such as below 1,000 Hz, and 25-40 dB at higher frequencies such as above 1,000 Hz.

Figure 2:
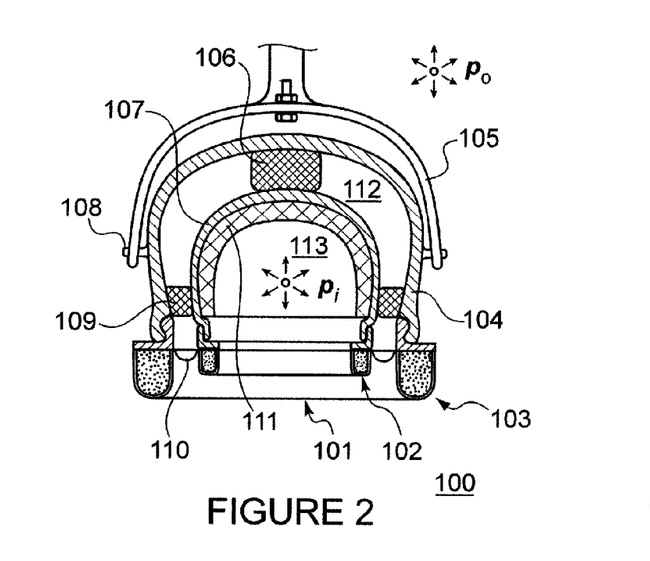
FIG. 2 illustrates a sound-attenuating earmuff assembly according to an embodiment comprising two rigid shells with the inner shell being positioned entirely within and mechanically isolated from the outer shell through a foam pad and an ear seal.

A sound-attenuating earmuff assembly 100 is illustrated in FIG. 2 in an exemplary embodiment. The earmuff assembly 100 comprises a cup-shaped, rigid outer shell 104, a cup-shaped, rigid inner shell 107 and a resilient ear seal 101. Each cup-shaped shell comprises three surfaces: an inner surface facing the wearer's head when the earmuff assembly is worn, an outer surface opposite to the inner surface and a peripheral surface extended between the circumferential edges of the outer and the inner surfaces. Both the outer and the inner shells may be made from plastic material. However, this is not meant as a limitation. The resilient ear seal 101 comprises an outer sealing ring 103 and an inner sealing ring 102 interconnected by a flexible thin skin layer 110. The outer sealing ring 103 and the inner sealing ring 102 are respectively fixed to the peripheral surfaces of the outer and the inner shells 104 and 107 and extend from the rigid shells to be in contact with the wearer's head. In the earmuff assembly 100, the flexible thin skin layer 110 acts as a vibration isolating/decoupling means to isolate/decouple the vibratory motions between the inner shell 107 and the outer shell 104. The earmuff assembly 100 may be mounted to a headband 105 in any desired manner, for example, through pivot pins 108 affixed on the outer side surface of the rigid outer shell 104. In an embodiment, the mounting means between the earmuff assembly 100 and the headband 105 allows the earmuff assembly 100 to pivot or rotate relative to the headband 105 for optimal positioning and maximum comfort as adjusted and perceived by the wearer. When in a loaded state, that is, when the earmuff assembly 100 is worn on the wearer's head, the headband 105 worn around the head provides a static clamping force to hold the earmuff assembly 100 in place.

In an embodiment illustrated in FIG. 2, the rigid inner shell 107 is positioned entirely within the rigid outer shell 104. An intermediate air gap 112 is then created between the inner surface of the rigid outer shell 104 and the outer surface of the rigid inner shell 107. Furthermore, the rigid inner shell 107 is centered in the rigid outer shell 104 by a foam spacer ring 109, comprising acoustic foam material although this is not meant as a limitation, and is constrained against upward slipping by the tapered contour of the rigid inner shell 107 and against downward slipping by the ear seal 101. To decouple vibratory motions between the two rigid shells, the inner shell 107 and the outer shell 104 are configured so as not to compress the foam spacer ring 109 in the loaded state. It will be understood that, while the specific embodiment employs a continuous spacer foam ring to position the rigid inner shell 107 within the rigid outer shell 104, this is not meant as a limitation. For example, a plurality of pliable pads of similar material in spaced intervals arranged circumferentially along the rigid inner shell 107 may be used in place of foam spacer ring 109. Alternatively, foam spacer ring 109 may be replaced by a layer of foam material disposed within the air gap 112. Since the spacer ring 109 is laterally inserted between and is not compressed by the rigid outer shell 104 and the rigid inner shell 107, it does not transmit either the headband clamping force or the noise-excited rigid-body vibration that is along the axial (vertical, as illustrated in FIG. 2) direction from the rigid outer shell 104 to the rigid inner shell 107. On the other hand, to provide maximum sound attenuation, both the rigid outer shell 104 and the rigid inner shell 107 are configured to maintain a circumferential close contact with the wearer's head by the clamping force provided by the headband 105.

According to an embodiment, in order to exert a static clamping force on the rigid inner shell 107, an elastic connector 106 is disposed in the intermediate air gap 112, between the rigid outer shell 104 and the rigid inner shell 107 and is aligned on the vertical axis of the two rigid shells. The elastic connector 106 comprises two ends with a first end (i.e., the top end as illustrated in FIG. 2) being adapted to contact the inner surface of the outer shell 104 and a second end (i.e., the bottom end as illustrated in FIG. 2) being adapted to contact the outer surface of the inner shell 107. In the loaded state, the clamping force provided by the headband 105 pushes the outer shell 104 and the outer sealing ring 103 toward the wearer's head. The outer shell 104 then pushes the first end of the elastic connector 106 and compresses the elastic connector 106 toward its second end where the inner shell 107 is connected. This compression procedure is finished in the loaded state when the headband force provided by the headband 105 is counterbalanced by the reaction force acting on the outer sealing ring 103 and the reaction force generated by the elastic connector 106 when it is being compressed. The latter force then acts as the static clamping force to push the inner shell 107 and the inner sealing ring 102 toward the wearer's head. In another embodiment, the elastic connector 106 is made from resilient materials having at least two stages of stiffness values depending on the load state, i.e., compression rate. For example, the elastic connector 106 presents a higher stiffness value in an initial stage when it is compressed within a certain percentage of its original length measured from its first end to its second end. After the initial stage, when the elastic connector 106 is compressed further into a secondary stage, the elastic connector 106 presents a stiffness value smaller and at least lower than that in the initial stage. The high stiffness in the initial stage is to ensure that, in the loaded state when the elastic connector 106 is preferably compressed into the secondary stage, the elastic connector 106 can provide a static clamping force that is sufficient to maintain close contact between the inner sealing ring 102 and the wearer's head. However when being exposed to external noise, the interconnecting pad 106 is also excited by a dynamic load in addition to the static load due to the clamping force. In this case, a low stiffness value of the elastic connector 106 helps to effectively isolate/decouple the vibratory motions between the outer shell 104 and the inner shell 107 since a high vibration isolation effectiveness usually requires a low stiffness spring to be used in the vibration isolation system.

The elastic connector 106 operates as a vibration isolating/decoupling means in the earmuff assembly 100 to isolate the inner shell 107 from the outer shell 104. In an embodiment, the elastic connector 106 is an interconnecting pad constructed of a urethane-based flexible foam material whose strain-stress relationship, i.e., the stiffness, is nonlinear and dependent on the load state. Such foam material has three stages of stiffness values under various compression rates. It typically presents high stiffness when it is compressed by less than 10-15%. In this compression percentage range, the foam material has good capability to sustain static load, i.e., the headband clamping force. When the compression rate is between 10% and 40%, the foam material presents low stiffness, which is ideal for vibration isolation. When the foam is compressed more than 40% of its original thickness, its stiffness becomes high again. The characteristics of the first two stages are leveraged in an elastic connector 106 comprising an interconnecting pad made from urethane-based flexible foam having nonlinear stiffness characteristics as described above such that the interconnecting pad is compressed by at least 10%, but no more than 40% by the inner shell 107 and the outer shell 104 in the loaded state. However, compressions of more than 40% will still give some attenuation and thus this range is not a limitation but is an exemplary embodiment only. Further, other materials may be used for the interconnecting pad, which materials may have different compression characteristics and thus potentially different compression ranges than the urethane foam. In other embodiments, the elastic connector 106 may be a spring or rubber connector.

When the earmuff assembly 100 is worn, i.e., in the loaded state, an ear of the wearer is enclosed in a cavity 113 defined by the rigid inner shell 107 that is interiorly lined with an acoustic foam insert 111. The foam insert 111 with suitable thickness and sound absorption capability will help dampen sound energy inside the acoustic cavity 113, particularly at higher frequencies, as disclosed in the prior art. The outer sealing ring 103 and the attached rigid outer shell 104 are compressed, by the headband force, into contact with the wearer's head surface to form a first layer of seal around the ear. Part of the headband force applied to the rigid outer shell 104 is then transmitted, through the elastic connector 106, to the rigid inner shell 107 and thus to the inner sealing ring 102 to form a second layer of seal around the ear. Therefore, a sound barrier is developed between the ear and the external noise sources. As will be understood by those skilled in the art, the pressure transmissibility (i.e., the inverse of the generally used term, sound attenuation performance) defined as the ratio of the acoustic pressure, $p_i$, inside the cavity 113 to the external acoustic pressure, $p_o$, of the earmuff assembly 100 can be theoretically predicted using a vibration model which is suitable for calculating sound attenuations of earmuff devices at low frequencies such as below 1,000 Hz.

Figure 3:
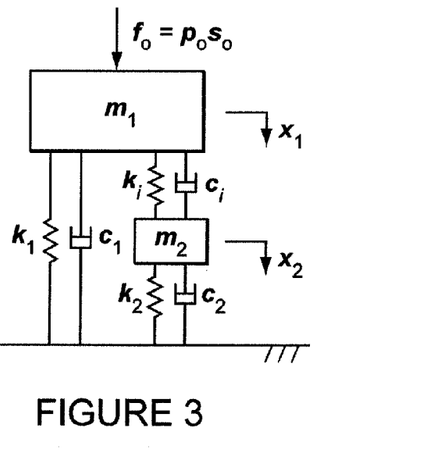
FIG. 3 illustrates a simplified vibration model according to an embodiment that is equivalent to the sound-attenuating earmuff assembly illustrated in FIG. 2 and is suitable for comparing the theoretical attenuation performance with that of a known single-walled earmuff at frequencies below about 1,000 Hz.

FIG. 3 illustrates a simplified vibration model which is equivalent to the sound-attenuating earmuff assembly illustrated in FIG. 2. The total mass of the outer rigid shell 104 and the outer sealing ring 103 is represented by mass $m_1$ while the total mass of the inner rigid shell 107 and the inner sealing ring 102 is represented by mass $m_2$. Mass $m_1$ is mounted to a rigid foundation representing the wearer's head through a spring with constant $k_1$ and a damping coefficient $c_1$ associated with the outer sealing ring 103 as well as the corresponding air spring. Likewise, mass $m_2$ is mounted to the rigid foundation through a spring with constant $k_2$ and a damping coefficient $c_2$ associated with the inner sealing ring 102 as well as the corresponding air spring. Because of the elastic connector 106, mass $m_2$ is also resiliently connected to mass $m_1$ through an intermediate spring with stiffness $k_i$ and damping coefficient $c_i$. The actual values of $k_i$ and $c_i$ are largely determined by the properties of the elastic connector 106. However, the spring stiffness and damping of the air gap 112 also contribute to $k_i$ and $c_i$. An exciting force $f_o$ generated by the external sound pressure $p_o$ acting upon an area, $s_o$, of the cross-section of the rigid outer shell 104 vibrates mass $m_1$. The vibration of mass $m_1$ is in turn transmitted to mass $m_2$ through the mechanical impedance represented by $k_i$ and $c_i$. The displacements of mass $m_1$ and mass $m_2$ are denoted as $x_1$ and $x_2$ in FIG. 3, respectively. According to the model, the acoustic pressure, $p_i$, within the cavity 113 and thus perceived by the wearer's ear is directly proportional to the amplitude of the displacement $x_2$.

Figure 4:
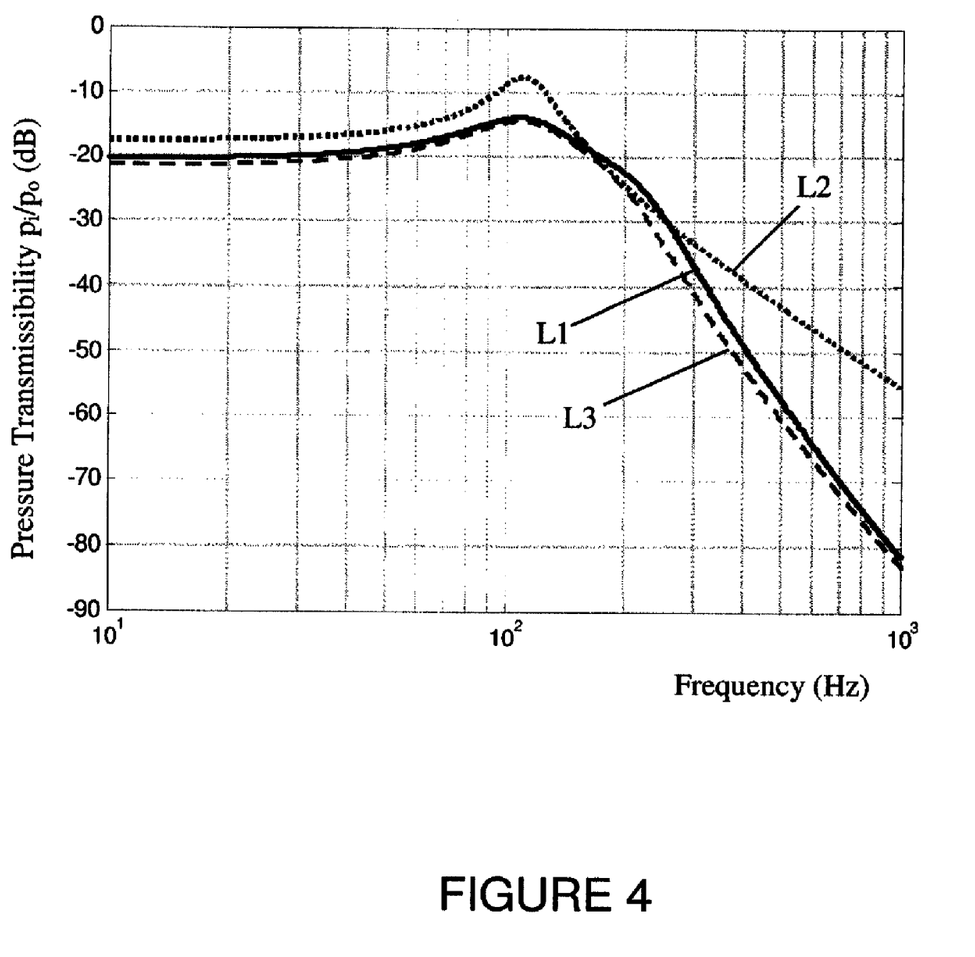
FIG. 4 is a graphical representation comparing the theoretical attenuation performance of the earmuff assembly having the isolated double-shell structure according to an embodiment to an earmuff having the single-walled shell structure.

FIG. 4 compares pressure transmissibility of various cases using the vibration model illustrated in FIG. 3. These comparisons are only made at frequencies below 1,000 Hz due to the limitations of the model. The solid line indicated by L1 in FIG. 4 is the theoretical pressure transmissibility of an earmuff having the isolated double-shell structure as illustrated in FIG. 2. The parameters used in predicting this curve were chosen to be practical and similar to what have been used by some of the prior art. The pressure transmissibility curve L1 may be compared to that of a conventional earmuff having identical mass, volume and cushion properties with the earmuff represented by L1. Such a conventional earmuff is referred to as the "reference" earmuff herein which is achieved by (a) removing the inner shell 107 and the elastic connector 106 from the earmuff assembly 100 illustrated in FIG. 2; (b) adding the mass of the original inner shell 107 to the outer shell 104, so that the mass of the single-walled cup of the reference earmuff equals the total mass of the inner shell 107 and the outer shell 104; and (c) combining the inner sealing ring 102 and the outer sealing ring 103 into a single sealing ring secured to the outer shell 104 so that the stiffness of the sealing ring of the reference earmuff is the sum of the stiffness of the inner sealing ring 102 and the outer sealing ring 103 of the present invention while the damping coefficient of the sealing ring of the reference earmuff is the same with the outer sealing ring 103.

The theoretical pressure transmissibility of the reference earmuff is predicted in FIG. 4 as the dotted line indicated by L2. According to the vibration model, there are resonance peak(s) on the transmissibility curve corresponding to the mode(s) of vibrating mass(es). For curve L1, two resonance peaks (at about 110 and 250 Hz) are observed since there are two vibrating masses, i.e., mass $m_1$ and mass $m_2$. For curve L2, one resonance peak (at about 120 Hz) is observed since there is only one vibrating mass whose weight equals the total weight of $m_1$ and $m_2$. Below the resonance region between 100 and 250 Hz, the transmissibility discrepancy between curve L1 and curve L2 is almost constant, with L1 slightly lower than L2. In the resonance region, L1 is lower than L2 at most frequencies except for frequencies around the highest resonance peak at about 250 Hz where L1 is higher than L2. Beyond the resonance region, the sound attenuating rate represented by curve L1 is much higher than that of the reference earmuff represented by curve L2.

In addition, at frequencies higher than 1,000 Hz where the sound attenuation performance of circumaural earmuffs is determined mainly by the flexural vibrations of the cup-shaped shells, the earmuff assembly illustrated in FIG. 2 also provides improved attenuation. This is because the flexural vibrations of the outer shell 104 excited by the external noise field can not be transmitted to the inner shell 107 effectively through the intermediate air gap 112 due to the impedance mismatch between the intermediate air gap 112 and the outer shell 104 and inner shell 107. Thus, the sound attenuation performance is maximized in a broad frequency range by minimizing the amplitudes of both the rigid body vibration and the flexural vibration of the inner shell 107, thus minimizing the sound level inside the cavity 113 where the wearer's ear is enclosed.

The dashed line indicated by L3 in FIG. 4 is the pressure transmissibility of the same case as L1 except that the intermediate spring stiffness used in calculating curve L3 is half of the value used in calculating curve L1. Comparing curve L3 to curve L1, it is seen that the sound attenuation performance is further improved when the intermediate spring stiffness is reduced. In an embodiment, the volume enclosed by the inner shell 107 is between 60% and 85% of the volume enclosed by the outer shell 104.

Figure 5A:
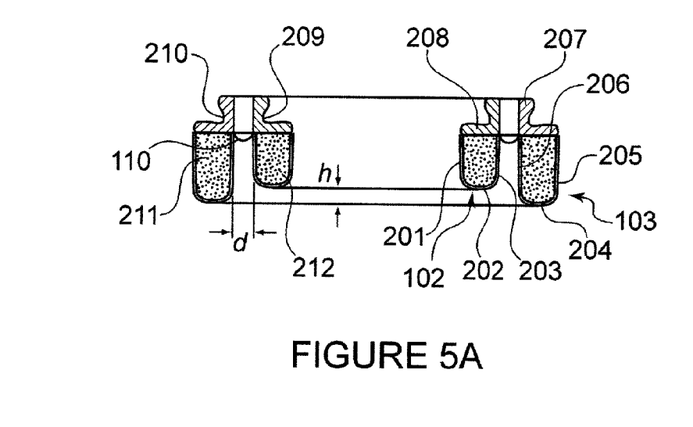
FIGS. 5A and 5B illustrate a cross-sectional view and a top view of the detailed structure of the ear seal according to the embodiment illustrated in FIG. 1.
Figure 5B:
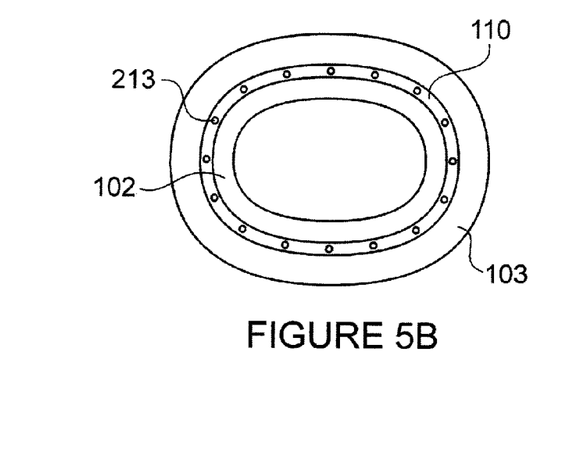
Figure 5C:
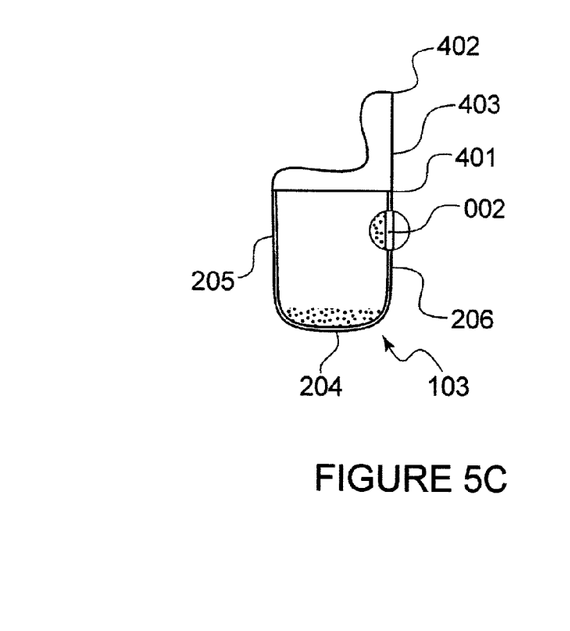
FIG. 5C illustrates an enlarged cross-sectional view of an outer sealing ring according to an embodiment comprising a flexible sheath and an "L" shaped rigid retainer plate.

FIGS. 5A and 5B illustrate a cross-sectional view and a top view respectively of the detailed structure of the ear seal integrated in the earmuff assembly 100 as illustrated in FIG. 2. With reference to the drawings and by way of illustration and not as a limitation, the ear seal comprises a resilient outer sealing ring 103 and a resilient inner sealing ring 102 positioned concentrically and interconnected by a ring-shaped flexible thin skin layer 110 which also acts as the vibration isolating/decoupling means between the inner shell and the outer shell in the earmuff assembly 100. Since the structures of the outer sealing ring 103 and the inner sealing ring 102 are identical, for illustration purposes, FIG. 5C only illustrates an enlarged cross-sectional view of the outer sealing ring. The annular outer sealing ring 103 comprises a first flexible sheath 002 and a first rigid retainer plate 207 (FIG. 5A). The first flexible sheath is generally made from a soft compliant material and is filled and in contact with cushioning material 211. The cushioning material may be foam or a silicon compound or a combination of both. It will be understood by those skilled in the art that other cushioning materials may also be suitable for this use. The first flexible sheath has a basic rectangular shape in cross-section and four surfaces: an annular exposed surface 204 adapted to contact the wearer's head, an annular base surface opposite to the annular exposed surface adapted to engage with the first rigid retainer plate 207 (FIG. 5A), an outer side surface 205 and an inner side surface 206. The first rigid retainer plate 207 (FIG. 5A) is generally made from rigid plastic material and is "L" shaped in cross-section. The first rigid retainer plate 207 (FIG. 5A) is provided with a base surface which is adapted to match with and bonded to the base surface of the first flexible sheath through means such as adhesive, high-frequency welding or thermoforming. The first rigid retainer plate 207 (FIG. 5A) is also provided with a vertical free surface 403 adjacent to its base surface and extends between an upper peripheral edge 402 and a lower peripheral edge 401.

Referring again to FIG. 5A, on the surface opposite the vertical free surface of the first rigid retainer plate 207 is a circumferential groove 209 that mates with the protrusion on the peripheral edge of the outer shell 104 and is for securing the outer sealing ring 103 to the outer shell 104. The annular inner sealing ring 102 comprises a second flexible sheath (not illustrated) comparable to first flexible sheath 002 (FIG. 5C) and a second rigid retainer plate 208. The second flexible sheath is generally made from a soft compliant material and is filled with and in contact with cushioning material 212. The cushioning material 212 may be foam or the silicon compound or a combination of both and is not necessarily the same as the cushion material 211. The second flexible sheath has a basic rectangular shape in cross-section and four surfaces: an annular exposed surface 202 adapted to contact the wearer's head, an annular base surface opposite to the annular exposed surface adapted to engage with the second rigid retainer plate 208, an outer side surface 203 and an inner side surface 201. The second rigid retainer plate 208 is generally made from rigid plastic material and is "L" shaped in cross-section. The second rigid retainer plate 208 is provided with a base surface which is adapted to match with and bonded to the base surface of the second flexible sheath through means such as adhesive, high-frequency welding or thermoforming. Facing directly the vertical free surface 403 of the first rigid retainer plate 207, there is a corresponding vertical free surface (not illustrated in FIG. 5C) of the second rigid retainer plate 208 which is adjacent to the base surface of the second rigid retainer plate 208 and extends between an upper peripheral edge and an lower peripheral edge (both edges are not illustrated in FIG. 5C). On the surface opposite to the vertical free surface of the second rigid retainer plate 208, there is a circumferential groove 210 that mates with the protrusion on the peripheral edge of the inner shell 107 and is for securing the inner sealing ring 102 to the inner shell 107.

Referring to FIG. 5A, the inner side surface 206 of the first flexible sheath and the vertical free surface of the first retainer plate 207 form an inner peripheral surface of the outer sealing ring 103. Likewise, the outer side surface 203 of the second flexible sheath and the vertical free surface of the second retainer plate 208 form an outer peripheral surface of the inner sealing ring 102. Finally, the inner sealing ring 102 and the outer sealing ring 103 are interconnected by a flexible thin skin layer 110 comprising an outer peripheral edge terminated at the inner peripheral surface of the outer sealing ring 103 and an inner peripheral edge terminated at the outer peripheral surface of the inner sealing ring 102. The flexible thin skin layer 110 is provided here to (a) retain the inner shell 107 within the outer shell 104 to form an integrated earmuff assembly, and (b) offer a flexible link to isolate/decouple vibratory forces or motions in the vertical axis direction between the outer shell 104 and the inner shell 107.

In the assembled position as illustrated by FIG. 5A, the inner sealing ring 102 is spaced from the outer sealing ring 103 by a distance of d circumferentially. In an embodiment, d ranges from 2 mm to 5 mm. If d is too small, there may not be enough clearance to ensure that the inner sealing ring-inner shell substructure does not contact the outer sealing ring-outer shell substructure during vibratory motions induced by the external noise. On the other hand, a d larger than the described range leads to a larger dimension of the outer sealing ring 103, which in turn makes it difficult to achieve a good seal since the contour of the head surface becomes more and more irregular farther away from the center of the ear canal. In another embodiment, the height of the outer sealing ring 103 is greater than the height of the inner sealing ring 102 by an amount of h. Thus, h represents the distance between the exposed surface and the corresponding base surface of the first or the second flexible sheath. In yet another embodiment, h varies circumferentially between 0 and 10 mm following the contour of the head surface around the ear. For example, h may be 0 for the part contacting the head surface in front of the ear towards the face of the wearer while h may have a higher value for the part contacting the head surface behind the ear towards the nape of the wearer.

In another embodiment illustrated in FIG. 5A, the flexible thin skin layer 110 is attached to extend between the inner peripheral edge of the base surface (i.e., the edge shared between the base surface and the inner side surface) of the first flexible sheath and the outer peripheral edge of the base surface (i.e., the edge shared between the base surface and the outer side surface) of the second flexible sheath. The attachment may be achieved through any desired means such as adhesive or thermoforming. In an embodiment, the width of the flexible thin skin layer 110 is at least 1.5 times larger than the distance d to prevent tension generated within the flexible thin skin layer 110 due to the relative vibratory motions of the outer shell 104 and the inner shell 107. In yet another embodiment, the flexible thin skin layer 110 is vented with holes 213 (FIG. 5B) distributed circumferentially to allow air trapped within the air gap 112 to escape when the earmuff assembly 100 is pressed toward the wearer's head. For similar reasons, both the inner sealing ring 102 and the outer sealing ring 103 are each provided with at least one vent hole for pressure release.

Figure 5D:
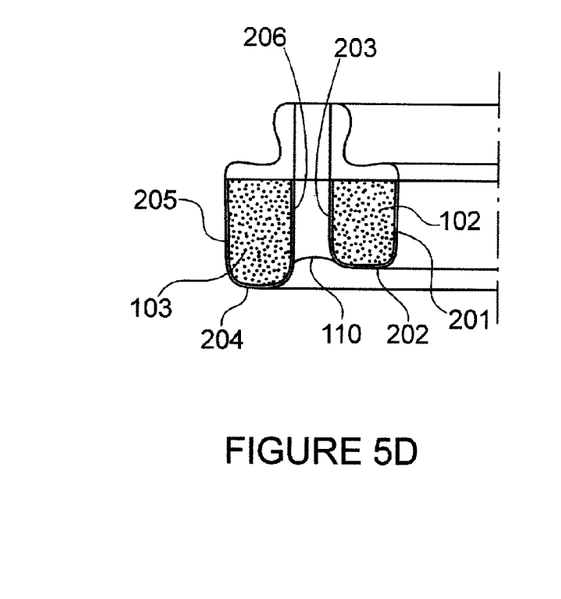
FIG. 5D illustrates an ear seal according to the embodiment illustrated in FIG. 5A where the flexible thin skin layer is attached to the two sealing rings at positions close to their open surfaces.

FIG. 5D illustrates another embodiment of the ear seal used in the earmuff assembly 100 as illustrated in FIG. 2 where the inner peripheral edge of the flexible thin skin layer 110 is alternatively attached to the outer side surface 203 of the second flexible sheath at a distance within 3 mm away from the exposed surface 202 of the second flexible sheath. The outer peripheral edge of the flexible thin skin layer 110 is then attached to the inner side surface 206 of the first flexible sheath so that the flexible thin skin layer 110 is parallel to the exposed surface 202 of the second flexible sheath. As adopted by the vibration model illustrated in FIG. 3, the head surface of the wearer can be practically approximate to a rigid foundation that does not undergo vibrations. Therefore, the exposed surfaces (202 and 204) of the inner sealing ring 102 and the outer sealing ring 103 that maintain contact with the wearer's head in the loaded state do not vibrate either. This implies that no or little relative motion between the inner sealing ring 102 and the outer sealing ring 103 occurs at positions on and close to their exposed surfaces, therefore no tension can be induced within the flexible thin skin layer 110 if it is attached at a position close to the exposed surfaces (202 and 204) of the sealing rings. This in turn implies that a flexible thin skin layer with a width the same as or smaller than the width indicated by d can be used. A smaller width of the flexible thin skin layer 110 will help to reduce the size of the outer sealing ring so that a better seal quality can be achieved. As explained previously, this is because the surface of the head more approximates a flat surface close to the ear and it is easier to seal to a flat surface than an irregular one.

Figure 6A:
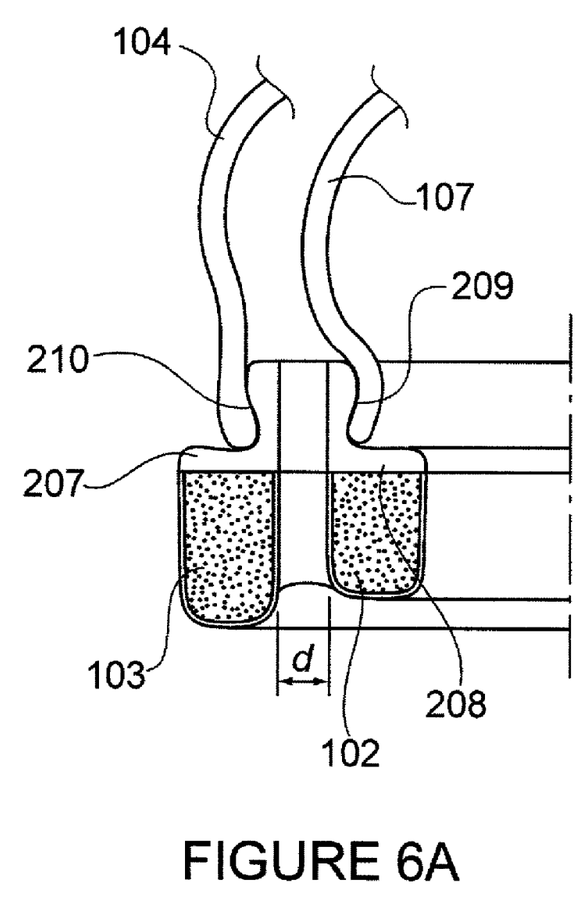
FIGS. 6A and 6B illustrate embodiments for attaching the ear seal to the two rigid shells.
Figure 6B:
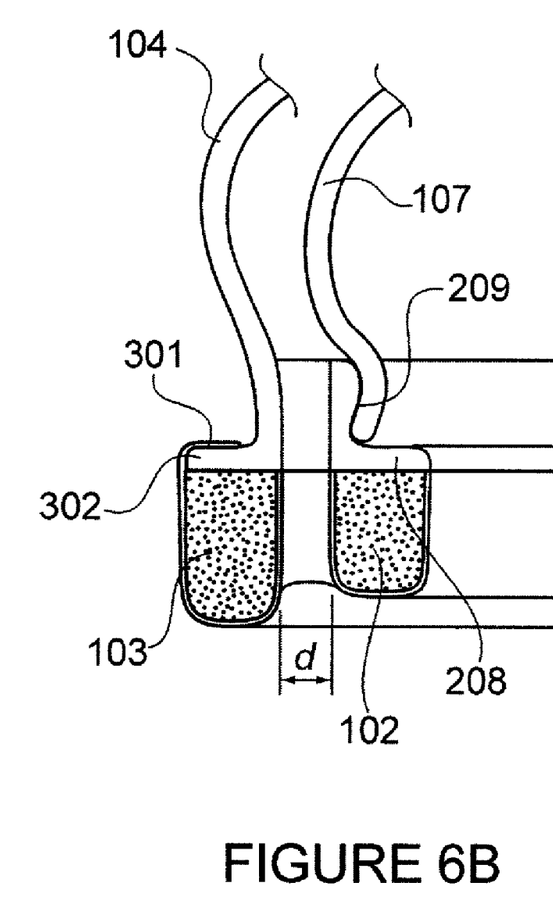

To be able to replace an ear seal as necessary during use, the two sealing rings of the ear seal should not be permanently affixed to the corresponding rigid shells. FIGS. 6A and 6B illustrate two possible embodiments for attaching the ear seal to the two rigid shells. In FIG. 6A, a circumferential groove indicated by 209 and 210 is cut into the vertical portion of the inner retainer plate 208 and the outer retainer plate 207, respectively. The mating edges of the inner shell 107 and the outer shell 104 are provided with protrusions in accordance with the contour of the grooves on the corresponding retainer plates. When the protrusions on the inner and the outer shells are forced into the grooves on the retainer plates of the inner and the outer sealing rings, they are clamped within the latter.

FIG. 6B illustrates another embodiment for attaching the outer sealing ring 103 to the outer shell 104. A retaining flap 301 is provided to engage the outer sealing ring 103 to the lip ring 302 provided by the outer shell 104. In this case, the rigid retainer plate 207 of the outer sealing ring is no longer necessary and is replaced with the flexible flap 301. Note in FIG. 6B, the inner sealing ring 102 is attached to the inner shell 107 using the groove-protrusion pair, i.e., press-fit style, as illustrated in FIG. 6A. It will be understood by those skilled in the art that, while the specific embodiment employs the press-fit style and the flap-flange style, other attachment or engagement means between the ear seal and the two rigid shells may also be used.

Figure 7:
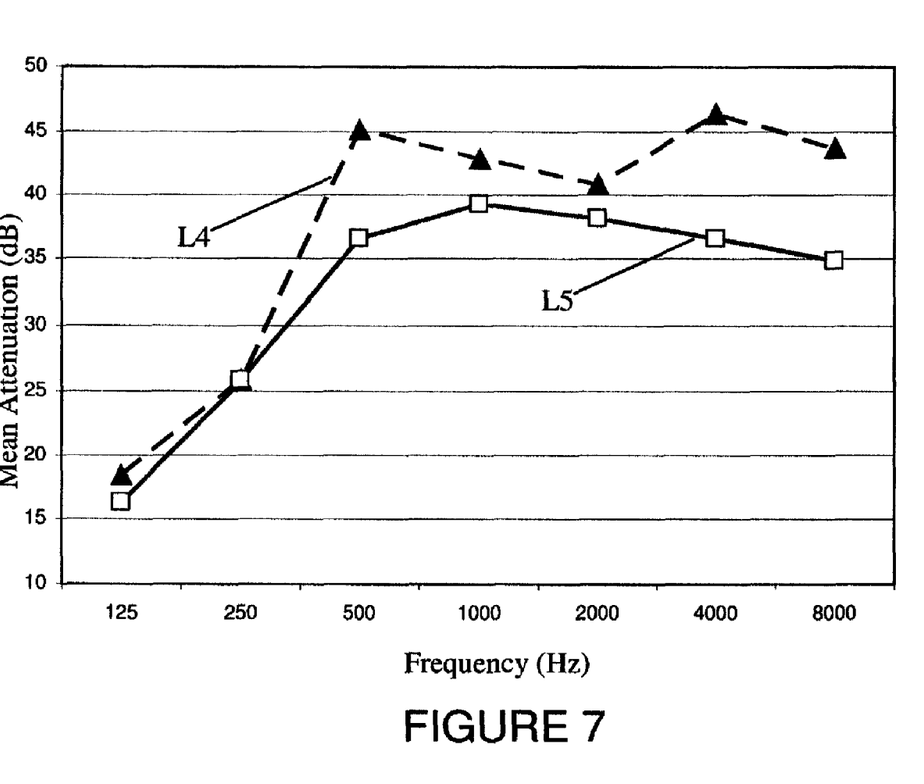
FIG. 7 is a graphical representation of experimental Real-EAR-At-Attenuation (REAT) data of an earmuff constructed according to the embodiment illustrated in FIG. 2 in comparison with a large volume earmuff having the single-walled structure known by prior art.

The sound attenuation performance of hearing protectors can be measured objectively using a Real-Ear-At-Threshold (REAT) method as described by ANSI standard S3.19-1974. Although not fully in accordance with the standard requirements (e.g., nine subjects were used instead of 10 as specified by the standard), a REAT test was conducted to compare the attenuation performance of the current invention and the conventional single-walled earmuff. Curve L4 in FIG. 7 is the experimental REAT attenuation data of an isolated double-shell earmuff constructed according to the embodiment as illustrated in FIG. 2. The experimental REAT attenuation data of a conventional single-walled earmuff known by the prior art is plotted as curve L5 in FIG. 7. Both curves are mean attenuations averaged over nine subjects and measured from 125 Hz to 8,000 Hz. To ensure that the results are comparable and illustrative, the enclosed volume and the weight of the conventional earmuff chosen for the experiments are similar to those of the double-shell earmuff constructed in accordance with embodiments described herein. In addition, both earmuffs shared an identical headband in the experiments so as to achieve the same static clamping force for both earmuffs when worn by test subjects.

Comparing curve L4 with curve L5, it is seen that, at frequencies above about 300-400 Hz, the mean sound attenuation achieved by the cup-shaped outer shell mounted on a resilient outer sealing ring and a cup-shaped inner shell mounted on a resilient inner sealing ring is significantly higher than that achieved by the conventional earmuff. At low frequency bands (i.e. 125 Hz and 250 Hz), the present invention performed slightly better than the conventional earmuff.

The experimental results are consistent with the analytical predictions presented in FIG. 4.

Figure 8:
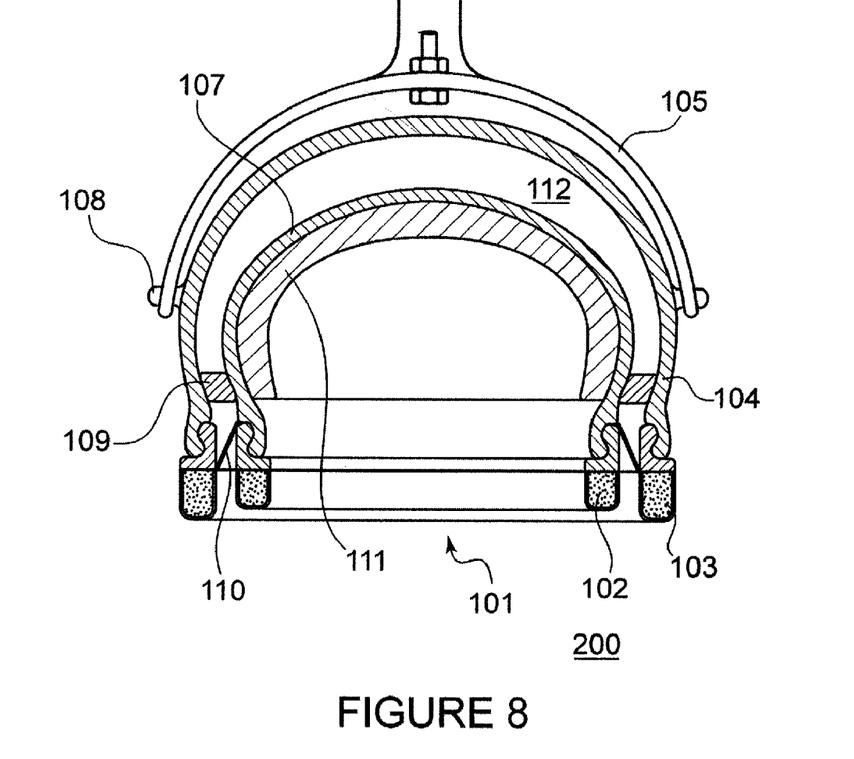
FIG. 8 illustrates a sound-attenuating earmuff assembly according to an embodiment comprising two rigid shells with the inner shell being positioned entirely within and mechanically isolated from the outer shell through an ear seal.

As illustrated in FIG. 4, the sound attenuation performance can be further improved when the intermediate spring stiffness between the two rigid shells is reduced. To reduce the intermediate spring stiffness, an ideal situation would be that there is no mechanical link between the outer shell and the inner shell. FIG. 8 illustrates a cross-sectional view of a sound-attenuating earmuff assembly 200 comprising a rigid inner shell 107 and a rigid outer shell 104 with the inner shell being positioned entirely within the outer shell through a resilient ear seal 101. Comparing the earmuff assembly 100 illustrated in FIG. 2 with the earmuff assembly 200 illustrated in FIG. 8, it is seen that the two earmuff assemblies share most components but can be distinguished by two features. First, the earmuff assembly 200 does not include elastic connector 106 as used in the earmuff assembly 100. This is intended to reduce the mechanical stiffness interacted between the inner shell 107 and the outer shell 104. Second, the flexible thin skin layer 110 between the inner sealing ring 102 and the outer sealing ring 103 is oriented and terminated differently in the earmuff assembly 100 and the earmuff assembly 200. Since the earmuff assembly 200 does not contain an elastic connector 106 that transmits the static headband clamping forces from the outer shell 104 to the inner shell 107, the flexible thin skin layer 110 in the earmuff assembly 200 will act as the means for applying headband clamping forces to the inner shell to keep it in contact with the wearer's head.

Figure 9:
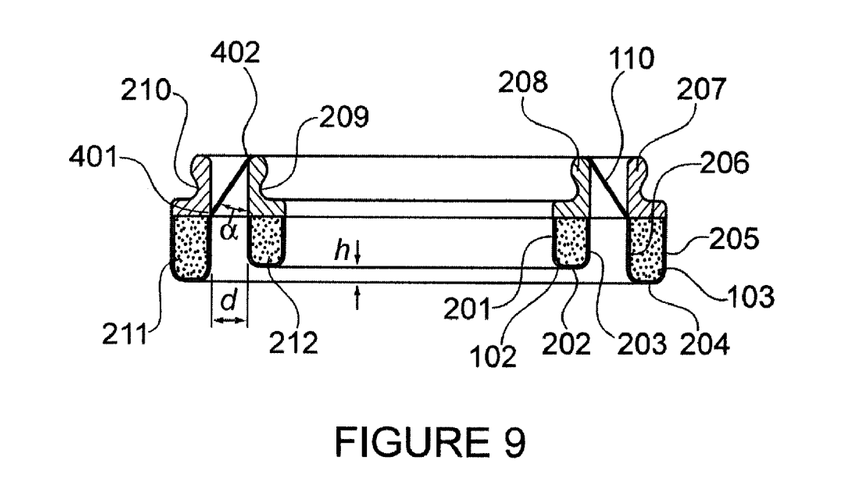
FIG. 9 illustrates a cross-sectional view of the detailed structure of the ear seal of the embodiment illustrated in FIG. 8.

FIG. 9 illustrates a cross-sectional view of the detailed structure of the ear seal according to FIG. 8. Same as the ear seal illustrated in FIG. 5A, the ear seal in FIG. 9 comprises an outer sealing ring 103 and an inner sealing ring 102 positioned concentrically and interconnected by a ring-shaped flexible thin skin layer 110. The annular outer and inner sealing rings comprise a first flexible sheath and a second flexible sheath, respectively. Both flexible sheaths are filled with cushioning material (211 and 212), such as foam or a silicon compound or a combination of both. The first flexible sheath is bonded to a first rigid retainer plate 207 while the second flexible sheath is bonded to a second rigid retainer plate 208. Both the first and the second rigid retainer plates are provided with means for engaging the sealing ring to the corresponding rigid shell. In the assembled position as illustrated in FIG. 9, the inner sealing ring 102 is spaced from the outer sealing ring 103 by a distance of d circumferentially. In an embodiment, d ranges from 2 mm to 5 mm. In yet another embodiment, the outer peripheral edge of the flexible thin skin layer 110 is terminated at the lower peripheral edge 401 on the vertical free surface of the first retainer plate 207, while the inner peripheral edge of the flexible thin skin layer 110 is terminated at the upper peripheral edge 402 on the vertical free surface of the second retainer plate 208. An acute angle, α, is then defined by the plane along which the flexible thin skin layer 110 is stretched and the vertical free surface of either the outer retainer plate 207 or the inner retainer plate 208.

In an embodiment, the height of the outer sealing ring 103 is greater than the height of the inner sealing ring 102 by an amount of h. In another embodiment, h varies circumferentially between 0 and 10 mm as dictated by the contour of the head surface around the ear. For example, h may be 0 for the part contacting the head surface in front of the ear towards the front face of the wearer while h may have a higher value for the part contacting the head surface behind the ear towards the nape of the wearer. When the earmuff assembly 200 is in the loaded state, both the outer sealing ring 103 and the inner sealing ring 102 will be compressed to the wearer's head and tension will be generated within the flexible thin skin layer 110 because of the way it is oriented. This tension provides static clamping force to the inner shell 107 to keep it in contact with the wearer's head and to maintain a good seal between the inner shell 107 and the wearer's head.

Figure 10A:
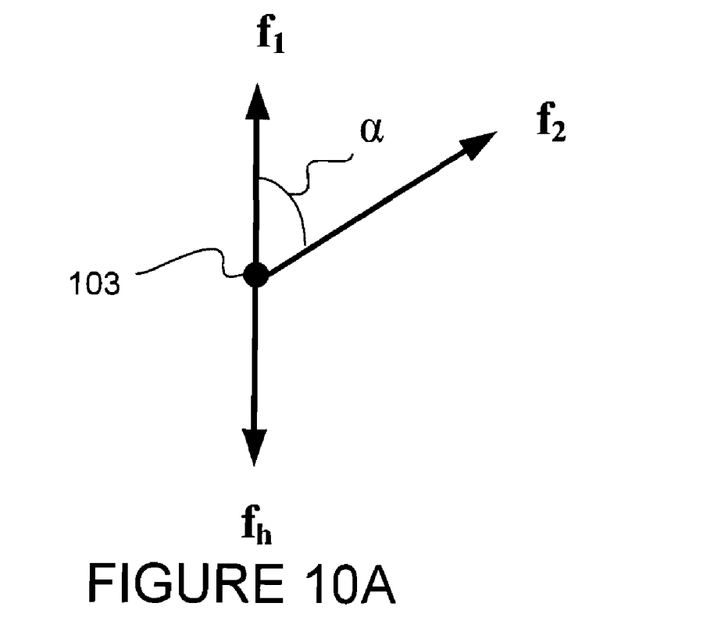
FIGS. 10A and 10B illustrate free-body-diagrams of the outer shell-seal substructure and the inner shell-seal substructure according to embodiments at the equilibrium position (i.e., loaded position on the wearer's head).
Figure 10B:
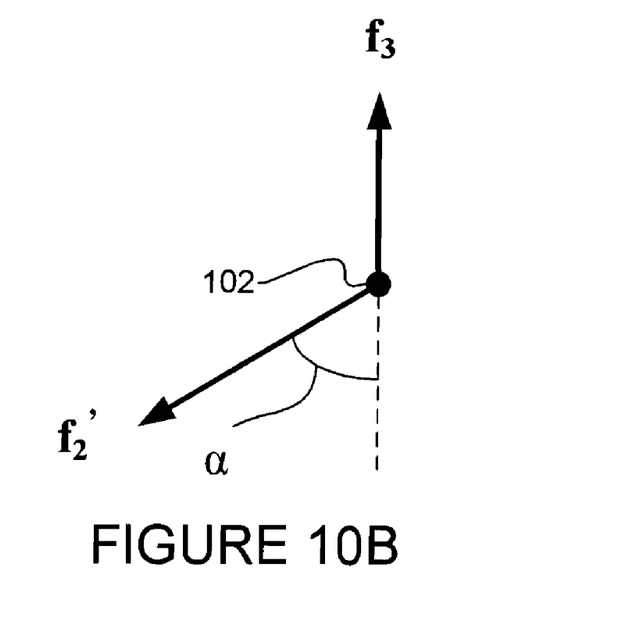

FIGS. 10A and 10B illustrate free-body-diagrams (FBD) illustrating the relationship between the static headband clamping forces and the static tension within the flexible thin skin layer 110 in the embodiment exemplified by FIG. 9. FIG. 10A shows the FBD of the outer sealing ring 103 in which $f_h$ is the clamping force provided by the headband 105, $f_1$ is the reaction force from the head surface to the outer sealing ring 103 and $f_2$ is the static tension force generated within the flexible thin skin layer 110. The force equilibrium relation in the vertical direction for the outer sealing ring 103 can then be written as:

$$f_h = f_1 + f_2 \cos \alpha \quad (1)$$

Similarly, FIG. 10B shows the FBD of the inner sealing ring 102 in which $f'_2$ is the reaction tension force equal to $f_2$ in amplitude and $f_3$ is the reaction force from the head surface to the inner sealing ring 102. The force equilibrium relation in the vertical direction for the inner sealing ring 102 can then be written as:

$$f_3 = f'_2 \cos \alpha \quad (2)$$

From Equation (2), it is found that a small angle $\alpha$ leads to higher reaction force, i.e., the clamping force, which can be applied to the inner shell 107. This in turn leads to better seal quality between the inner shell 107 and the wearer's head. In an embodiment, $\alpha$ is smaller than 30°. It is easily understood that, in order to form a good seal at the interface between the user's head and both the inner sealing ring 102 and the outer sealing ring 103, neither $f_1$ nor $f_3$ can be zero. A further analysis shows that the amplitudes of $f_1$ and $f_3$ are determined by the compression rates of the outer sealing ring 103 and the inner sealing ring 102. In yet another embodiment, parameters are used to compose the ear seal having structures illustrated in FIG. 9 such that, in the loaded state, the resulting clamping force on the outer shell 104 and the inner shell 107 have the following relation:

$$f_1 = f_3 = f_2 \cos \alpha = \frac{1}{2} f_h \quad (3)$$

It will be understood by those skilled in the art that the structures and methods described herein may be embodied in other specific forms without departing from the scope of this disclosure and that the examples and embodiments described herein are in all respects illustrative and not restrictive. Those skilled in the art will recognize that other embodiments using the concepts described herein are also possible. Further, any reference to claim elements in the singular, for example, using the articles "a," "an," or "the," is not to be construed as limiting the element to the singular. Moreover, a reference to a specific time, time interval, and instantiation of scripts or code segments is in all respects illustrative and not limiting.

What is claimed is:

1. A sound-attenuating earmuff assembly for circumaural hearing protection headsets, comprising:
    a cup-shaped rigid outer shell;
    a cup-shaped rigid inner shell, wherein the inner shell is smaller than, and resides entirely within, the outer shell and wherein an inner surface of the outer shell and an outer surface of the inner shell define an intermediate air gap;
    an ear seal having an outer sealing ring and an inner sealing ring, wherein the outer sealing ring is attached to the outer shell and the inner sealing ring is attached to the inner shell; and
    a resilient elastic connector connecting the inner shell to the outer shell, wherein the resilient elastic connector is fabricated from a material selected to dynamically decouple the inner shell from the outer shell in proportion to a measure of stiffness of the selected material.

2. The sound-attenuating earmuff assembly of claim 1 further comprising:
    a headband attached to the cup-shaped rigid outer shell, wherein when worn by a user the headband provides a static clamping force to the sound attenuating earmuff directed to the user's head.

3. The sound-attenuating earmuff assembly of claim 1 further comprising a foam spacer interposed within the intermediate air gap positioning the inner shell at the center of the outer shell, wherein a volume of the foam spacer is less than a volume of the intermediate air gap.

4. The sound-attenuating earmuff assembly of claim 3, wherein the foam spacer is selected from the group consisting of a foam layer, a foam ring or a plurality of foam pads arranged circumferentially in spaced intervals in the intermediate air gap.

5. The sound-attenuating earmuff assembly of claim 1, wherein a volume enclosed by the inner shell is 60% to 85% of a volume enclosed by the outer shell.

6. The sound-attenuating earmuff assembly of claim 1, wherein the resilient elastic connector comprises a resilient interconnecting pad made from a resilient material having first and second stiffness values, wherein the first stiffness value is higher than the second stiffness value, and wherein a first stiffness value is presented when the elastic connector is compressed within a certain percentage of its original length and wherein the second stiffness value is presented when the resilient interconnecting pad is compressed further.

* * * * *